(12) United States Patent
Bangera et al.

(10) Patent No.: US 9,101,743 B2
(45) Date of Patent: *Aug. 11, 2015

(54) FLUID SPRAYING APPARATUSES, AND RELATED SYSTEMS AND METHODS

(75) Inventors: Mahalaxmi Gita Bangera, Renton, WA (US); Roderick A. Hyde, Redmond, WA (US); Jordin T. Kare, Seattle, WA (US); Eric C. Leuthardt, St. Louis, MO (US); Lowell L. Wood, Jr., Bellevue, WA (US)

(73) Assignee: ELWHA, LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/462,203

(22) Filed: May 2, 2012

(65) Prior Publication Data

US 2013/0296811 A1 Nov. 7, 2013

(51) Int. Cl.
| A61M 35/00 | (2006.01) |
| A61B 18/02 | (2006.01) |
| A61B 18/04 | (2006.01) |
| A61B 19/00 | (2006.01) |

(52) U.S. Cl.
CPC ............ *A61M 35/00* (2013.01); *A61B 18/0218* (2013.01); *A61B 2018/046* (2013.01); *A61B 2019/461* (2013.01)

(58) Field of Classification Search
USPC ........................................................ 604/290
See application file for complete search history.

(56) References Cited

U.S. PATENT DOCUMENTS

| 3,534,739 | A | 10/1970 | Bryne |
| 4,043,341 | A | 8/1977 | Tromovitch |
| 4,348,873 | A | 9/1982 | Yamauchi et al. |
| 4,376,376 | A | 3/1983 | Gregory |
| 4,783,008 | A | 11/1988 | Ikeuchi et al. |
| 5,098,428 | A | 3/1992 | Sandlin et al. |
| 5,344,478 | A * | 9/1994 | Zurecki et al. .................. 75/709 |
| 5,814,040 | A | 9/1998 | Nelson et al. |
| 5,997,530 | A | 12/1999 | Nelson et al. |
| 6,027,499 | A | 2/2000 | Johnston et al. |
| 6,171,301 | B1 | 1/2001 | Nelson et al. |
| 6,173,916 | B1 | 1/2001 | Krone-Schmidt |
| 6,226,996 | B1 | 5/2001 | Weber et al. |
| 6,248,103 | B1 | 6/2001 | Tannenbaum et al. |

(Continued)

OTHER PUBLICATIONS

U.S. Appl. No. 13/478,370, filed May 23, 2012, Bangera, et al.

(Continued)

*Primary Examiner* — Tatyana Zalukaeva
*Assistant Examiner* — Guy K Townsend
(74) *Attorney, Agent, or Firm* — Dorsey & Whitney LLP

(57) ABSTRACT

Embodiments disclosed herein are directed to fluid spraying apparatuses, and related systems and methods. The disclosed fluid spraying apparatuses may be used, for example, to spray a medically suitable fluid on a target region of a subject, such as for treating or removing tissue of the subject. In an embodiment, a fluid spraying apparatus includes a spray mechanism including at least one reservoir, and a spraying device operably coupled to the at least one reservoir which has an adjustable spray nozzle. The fluid spraying apparatus includes a distance sensor configured to sense information at least related to a distance to a target region of a subject and output one or more signals encoding the information, and control electrical circuitry operably coupled to the spray mechanism and the distance sensor. The control electrical circuitry is configured to activate the spray mechanism responsive to receiving the one or more signals.

40 Claims, 11 Drawing Sheets

(56) References Cited

U.S. PATENT DOCUMENTS

| | | | |
|---|---|---|---|
| 6,514,244 B2* | 2/2003 | Pope et al. | 606/9 |
| 6,635,053 B1 | 10/2003 | Lalonde et al. | |
| 6,764,493 B1 | 7/2004 | Weber et al. | |
| 6,996,951 B2 | 2/2006 | Smith et al. | |
| 7,025,762 B2 | 4/2006 | Johnston et al. | |
| 7,255,693 B1 | 8/2007 | Johnston et al. | |
| 7,273,479 B2 | 9/2007 | Littrup et al. | |
| 7,282,060 B2 | 10/2007 | DeBenedictis et al. | |
| 7,318,821 B2 | 1/2008 | Lalonde et al. | |
| 7,769,469 B2 | 8/2010 | Carr et al. | |
| 7,780,656 B2 | 8/2010 | Tankovich | |
| 7,921,657 B2 | 4/2011 | Littrup et al. | |
| 8,591,504 B2 | 11/2013 | Tin | |
| 2001/0009997 A1* | 7/2001 | Pope et al. | 606/9 |
| 2002/0143323 A1 | 10/2002 | Johnston et al. | |
| 2002/0161357 A1 | 10/2002 | Anderson et al. | |
| 2004/0002704 A1 | 1/2004 | Knowlton et al. | |
| 2005/0154380 A1* | 7/2005 | DeBenedictis et al. | 606/9 |
| 2005/0261753 A1 | 11/2005 | Littrup et al. | |
| 2006/0069306 A1 | 3/2006 | Banik et al. | |
| 2007/0118098 A1 | 5/2007 | Tankovich | |
| 2007/0276360 A1 | 11/2007 | Johnston et al. | |
| 2008/0071332 A1 | 3/2008 | Nelson et al. | |
| 2008/0119828 A1 | 5/2008 | Nelson et al. | |
| 2008/0173028 A1 | 7/2008 | Littrup et al. | |
| 2008/0287943 A1 | 11/2008 | Weber et al. | |
| 2009/0192505 A1 | 7/2009 | Askew et al. | |
| 2010/0057065 A1* | 3/2010 | Krimsky | 606/21 |
| 2010/0087806 A1 | 4/2010 | Da Silva et al. | |
| 2010/0111837 A1* | 5/2010 | Boyden et al. | 424/1.11 |
| 2010/0111846 A1* | 5/2010 | Boyden et al. | 424/1.29 |
| 2010/0111847 A1* | 5/2010 | Boyden et al. | 424/1.29 |
| 2010/0111848 A1* | 5/2010 | Boyden et al. | 424/1.29 |
| 2010/0111849 A1* | 5/2010 | Boyden et al. | 424/1.29 |
| 2010/0111850 A1* | 5/2010 | Boyden et al. | 424/1.29 |
| 2010/0111854 A1* | 5/2010 | Boyden et al. | 424/1.49 |
| 2010/0111855 A1* | 5/2010 | Boyden et al. | 424/1.49 |
| 2010/0111938 A1* | 5/2010 | Boyden et al. | 424/133.1 |
| 2010/0112067 A1* | 5/2010 | Boyden et al. | 424/489 |
| 2010/0112068 A1* | 5/2010 | Boyden et al. | 424/489 |
| 2010/0113614 A1* | 5/2010 | Boyden et al. | 514/769 |
| 2010/0113615 A1* | 5/2010 | Boyden et al. | 514/769 |
| 2010/0114348 A1* | 5/2010 | Boyden et al. | 700/97 |
| 2010/0114547 A1* | 5/2010 | Boyden et al. | 703/11 |
| 2010/0119557 A1* | 5/2010 | Boyden et al. | 424/400 |
| 2010/0121466 A1* | 5/2010 | Boyden et al. | 700/17 |
| 2010/0143243 A1* | 6/2010 | Boyden et al. | 424/1.29 |
| 2010/0152651 A1* | 6/2010 | Boyden et al. | 604/66 |
| 2010/0152880 A1 | 6/2010 | Boyden et al. | |
| 2010/0163576 A1* | 7/2010 | Boyden et al. | 222/71 |
| 2010/0168725 A1 | 7/2010 | Babkin et al. | |
| 2010/0168900 A1* | 7/2010 | Boyden et al. | 700/117 |
| 2010/0185174 A1* | 7/2010 | Boyden et al. | 604/503 |
| 2010/0187728 A1* | 7/2010 | Boyden et al. | 264/442 |
| 2010/0249765 A1 | 9/2010 | Johnston | |
| 2010/0274236 A1 | 10/2010 | Krimsky | |
| 2010/0286791 A1* | 11/2010 | Goldsmith | 623/23.7 |
| 2011/0024132 A1 | 2/2011 | Pettit | |
| 2011/0168808 A1 | 7/2011 | Mitch | |
| 2011/0230753 A1 | 9/2011 | Mahon et al. | |

OTHER PUBLICATIONS

PCT International Search Report; International App. No. PCT/US2013/039198; Aug. 15, 2013; pp. 1-2.

PCT International Search Report; International App. No. PCT/US2013/039202; Aug. 15, 2013; pp. 1-3.

* cited by examiner

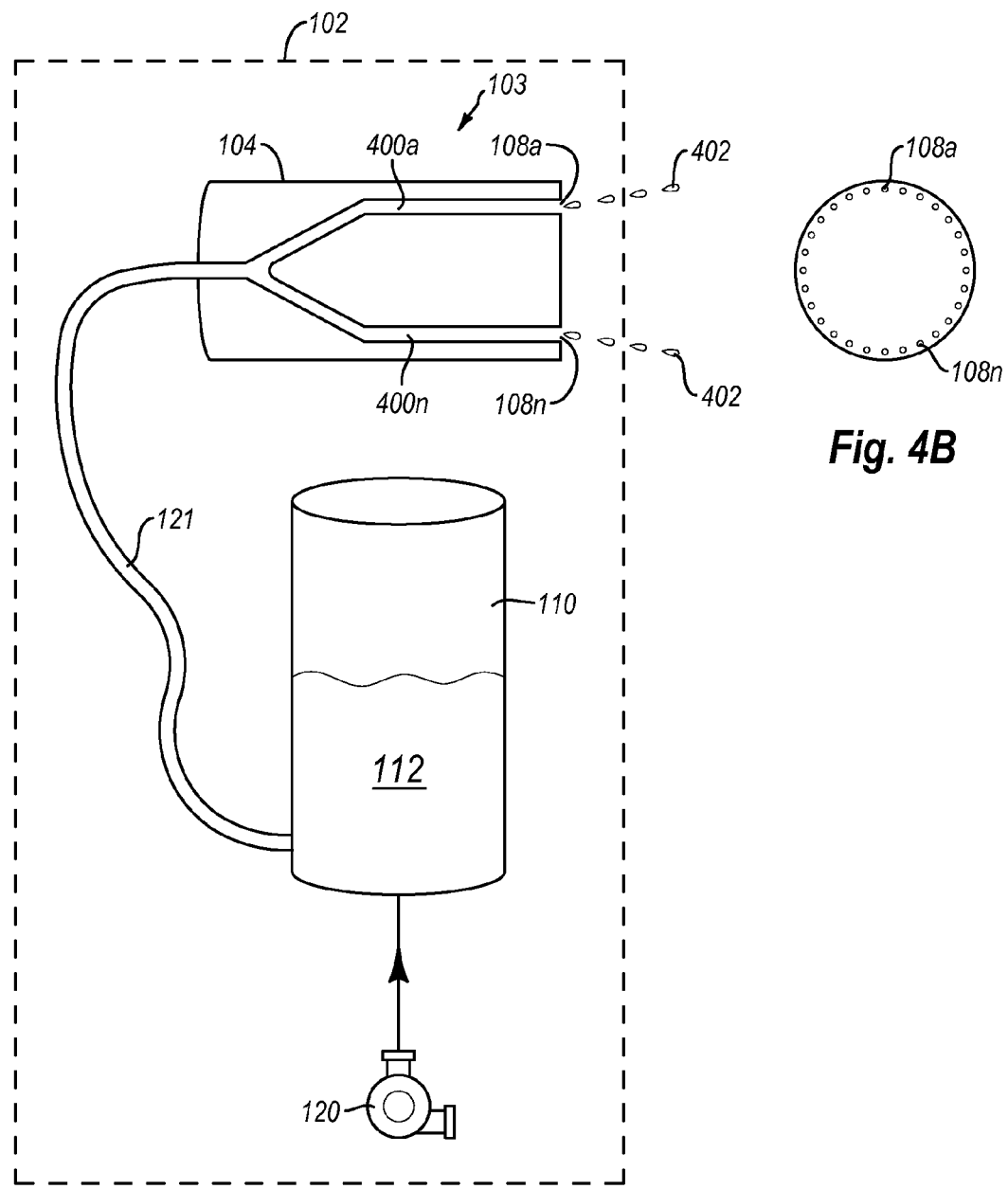
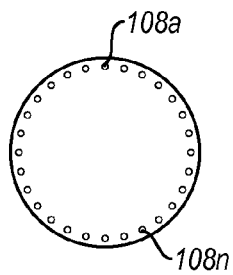
Fig. 4B
Fig. 4A

FLUID SPRAYING APPARATUSES, AND RELATED SYSTEMS AND METHODS

SUMMARY

Embodiments disclosed herein are directed to fluid spraying apparatuses, and related systems and methods. The disclosed fluid spraying apparatuses include at least one distance sensor and a spray mechanism that is controllable responsive to sensing feedback from the at least one distance sensor and other optional sensor(s). The disclosed fluid spraying apparatuses may be used, for example, to spray a medically suitable fluid on a target region of a subject, such as for treating or removing tissue from a subject.

In an embodiment, a fluid spraying apparatus includes a spray mechanism including at least one reservoir, and a spraying device operably coupled to the at least one reservoir which has an adjustable spray nozzle. The fluid spraying apparatus includes a distance sensor configured to sense information at least related to a distance to a target region of a subject and output one or more signals encoding the information, and control electrical circuitry operably coupled to the spray mechanism and the distance sensor. The control electrical circuitry is configured to activate the spray mechanism responsive to receiving the one or more signals.

In an embodiment, a method of adjusting a spray mechanism of a fluid spraying apparatus is disclosed. The method includes sensing, with a distance sensor, information at least related to a distance to a target region of a subject. The method further includes at least partially based on the information, adjusting the spray mechanism. The method additional includes spraying fluid onto the target region from the adjusted spray mechanism.

In an embodiment, a system is disclosed. The system includes a distance sensor configured to sense information at least related to a distance to a target region of a subject and output one or more signals encoding the information, and a fluid spraying apparatus operably coupled to the distance sensor. The fluid spraying apparatus includes a spray mechanism having at least one reservoir configured to hold fluid and a spraying device operably coupled to the at least one reservoir. The spraying device includes an adjustable spray nozzle. The system further includes a computer operably coupled to the spray mechanism and the distance sensor. The computer includes memory storing instructions for directly activating the spray mechanism responsive to receiving the one or more signals.

The foregoing is a summary and thus may contain simplifications, generalizations, inclusions, and/or omissions of detail; consequently, the reader will appreciate that the summary is illustrative only and is NOT intended to be in any way limiting. Other aspects, features, and advantages of the devices and/or processes and/or other living subject matter described herein will become apparent after reading the teachings set forth herein.

BRIEF DESCRIPTION OF THE FIGURES

FIG. 4A is a partial schematic diagram of the fluid spraying apparatus shown in FIG. 1 in which a spray mechanism includes a spray nozzle configured to spray droplets according to an embodiment.

FIG. 4B is a plan view of the adjustable spray nozzle shown in FIG. 4A.

DETAILED DESCRIPTION

Figure 1:
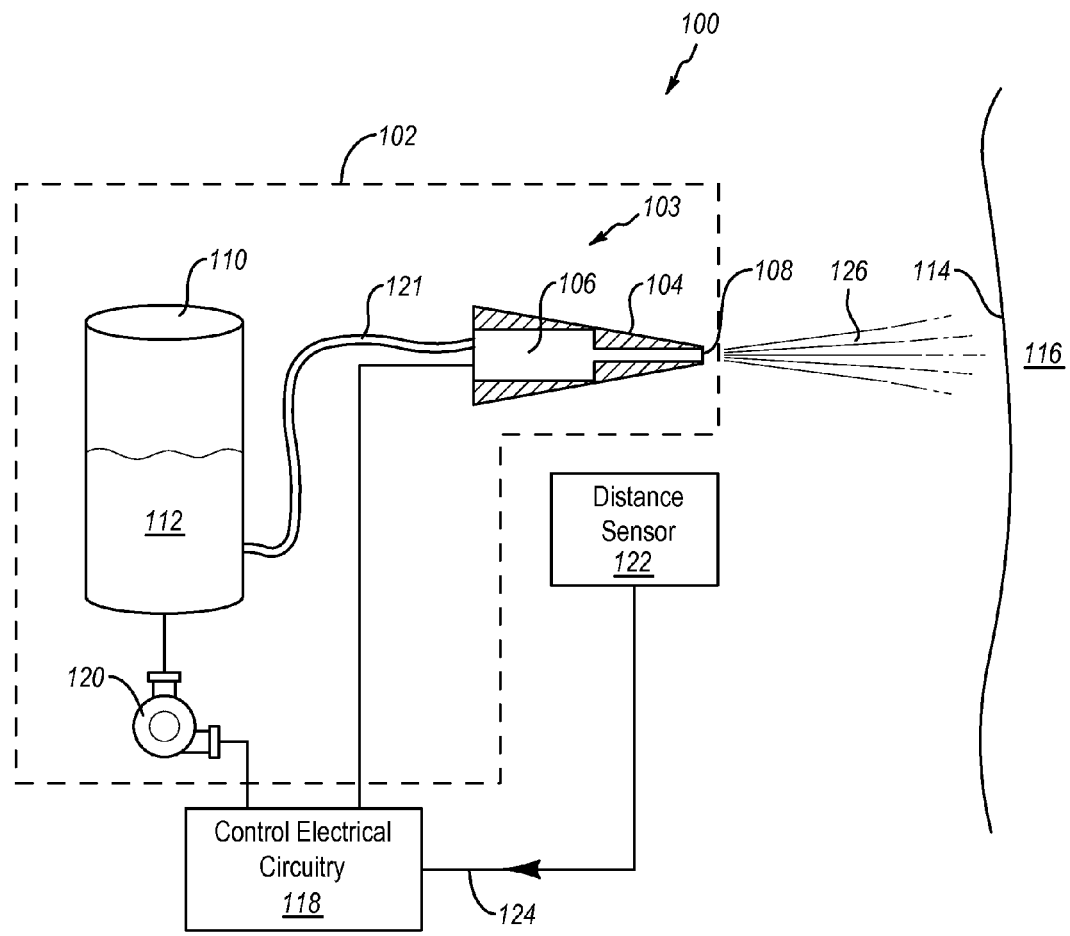
FIG. 1 is a schematic diagram of an embodiment of a fluid spraying apparatus.

Embodiments disclosed herein are directed to fluid spraying apparatuses, and related systems and methods. The disclosed fluid spraying apparatuses include at least one distance sensor and a spray mechanism that is controllable responsive to sensing feedback from the at least one distance sensor and other optional sensor(s). The disclosed fluid spraying apparatuses may be used, for example, to spray a medically suitable fluid on a target region of a subject, such as for treating or removing tissue from a subject during cryosurgery or pyrosurgery.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be strictly limiting. Other embodiments may be utilized, and other changes may be made, without departing from the spirit or scope of the subject matter presented herein.

FIG. 1 is a schematic diagram of an embodiment of a fluid spraying apparatus 100. The fluid spraying apparatus 100 is suitable for spraying a medically suitable fluid onto a target region of a subject for a variety of uses. For example, the sprayed fluid may be employed for treating or removing internal or external tissue of a subject. The fluid spraying apparatus 100 includes a spray mechanism 102 having a spraying device 103 with an adjustable spray nozzle 104 (e.g., an atomizing adjustable spray nozzle, a pressure-swirl spray nozzle, or other suitable nozzle). The adjustable spray nozzle 104 includes a fluid delivery passageway 106 extending therethrough that terminates at one end of the adjustable spray nozzle 104 as an output orifice 108 from which fluid may be sprayed.

The spray mechanism 102 of the fluid spraying apparatus 100 further includes at least one reservoir 110 holding a fluid 112 therein. For example, the reservoir(s) disclosed herein may be a canister, a flexible bag, a receptacle, or other suitable container for holding fluid. The fluid 112 may include at least one of a liquid, a gas, or an aerosol. As an example, the fluid 112 may include a cryogen or a fluid having a temperature greater than about 45° C. (i.e., a pyrofluid). Suitable examples of cryogen include at least one of nitrogen, carbon dioxide, a fluorocarbon, ethynol, or ethanol.

The reservoir 110 is in fluid communication with the fluid delivery passageway 106 of the adjustable spray nozzle 104 via one or more fluid conduits 121 (e.g., tubing or passageways formed in a substrate). The reservoir 110 is in fluid communication with the fluid delivery passageway 106 of the adjustable nozzle assembly 104 such that the fluid 112 may be received by the fluid delivery passageway 106 of the adjustable nozzle assembly 104 and sprayed from the output orifice 108 onto a target region 114 of a subject 116, such as a human or non-human animal subject. For example, the target region 114 may be internally or externally located on the subject 116.

The spray mechanism 102 further includes a pump 120 operably coupled to the reservoir 110 and control electrical circuitry 118 that functions as a controller. For example, the pump 120 may be configured as an electronically-activated pneumatic pump, an electronically-activated hydraulic pump, or an electronically-activated reciprocating pump (e.g., a plunger pump or a diaphragm pump). The pump 120 is configured to pump the fluid 112 from the reservoir 110 to the fluid delivery passageway 106 of the adjustable nozzle assembly 104 via the one or more fluid conduits 121. As will be discussed in more detail below, the control electrical circuitry 118 is also operably coupled to the adjustable spray nozzle 104, in addition to the pump 120, for controlling the operation thereof.

At least one distance sensor 122 is further operably coupled to the control electrical circuitry 118. For example, the distance sensor 122 may be at least one of a passive distance sensor or an active distance sensor. Examples of suitable passive distance sensors include an image sensor, such as an electronic camera, machine vision system, or other suitable electronic imaging device. For example, such an image sensor may be positioned and configured to image subsurface features of the target region 114, such as vasculature of the target region 114, which can be affected by a fluid spray from the spraying device 103. Examples of suitable active distance sensors include an acoustic sensor that is configured to output an acoustic signal to the target region 114 and receive a reflected acoustic signal therefrom, an ultrasonic sensor that is configured to output an ultrasonic signal to the target region 114 and receive a reflected ultrasonic signal therefrom, an optical sensor that is configured to output an optical signal to the target region 114 and receive a reflected optical signal therefrom, or a radar device that is configured to output an electromagnetic signal to the target region 114 and receive a reflected electromagnetic signal therefrom.

The distance sensor 122 is positioned and configured to sense information at least related to a distance that the spray mechanism 102 (e.g., the output orifice 108 of the adjustable spray nozzle 104) is from the target region 114 of the subject 116 and output one or more sensing signals 124 to the control electrical circuitry 118 indicative (e.g., encoding) of the information at least related to the distance.

In operation, the distance sensor 122 senses information at least related to a distance that the spray mechanism 102 is from the target region 114 of the subject 116 and outputs the one or more sensing signals 124 to the control electrical circuitry 118 indicative of the information at least related to the distance. The control electrical circuitry 118 determines one or more operational characteristics of the spray mechanism 102 (e.g., adjustable spray nozzle 104, at least one reservoir 110, or the pump 120) to be adjusted at least partially based on the information, adjusts the one or more operational characteristics of the spray mechanism 102 at least partially based on the determined one or more operational characteristics, and directs the adjusted spray mechanism 102 configured with the one or more adjusted operational characteristics to spray the fluid 112 as a spray 126 onto the target region 114 responsive to the pump 120 delivering the fluid 112 to the spray mechanism 102. For example, the one or more operational characteristics include at least one of pressure of the spray 126, droplet size of the spray 126, or geometry of the spray 126.

As further explained below, responsive to the one or more sensing signals 124, the control electrical circuitry 118 may direct altering a number of different operational characteristics of the spray mechanism 102. For example, during operation, the control electrical circuitry 118 may direct the adjustable spray nozzle 104 to alter a spray width of the spray 126 responsive to receiving the one or more sensing signals 124. As another example, during operation, the control electrical circuitry 118 may direct the pump 120 to alter a fluid pressure of the fluid 112 sprayed therefrom as the spray 126 responsive to receiving the one or more sensing signals 124. Altering the fluid pressure may be effected by increasing or decreasing the pressure exerted on the fluid 112 in the reservoir 110 by the pump 120. As yet another example, during operation, the control electrical circuitry 118 may direct the adjustable spray nozzle 104 to alter a fluid focus thereof responsive to receiving the one or more sensing signals 124. As yet another example, during operation, the control electrical circuitry 118 may direct the spray mechanism 102 to alter a droplet size of the spray 126 responsive to receiving the one or more sensing signals 124 by increasing or decreasing the pressure exerted on the fluid 112 in the reservoir 110 by the pump 120. As yet a further example, during operation, the control electrical circuitry 118 may direct adjusting the adjustable spray nozzle 104 to substantially maintain a target arrival diameter of the spray 126 responsive to receiving the one or more sensing signals 124.

The instructions that the control electrical circuitry 118 employs for directing and controlling operation of the spray mechanism 102, such as selected fluid focus, target arrival diameter, or other spray characteristics may be pre-programmed in the control electrical circuitry 118 without user input or programmed by the user. For example, the programming may be effected via at least one of software, firmware, programmable logical devices, or other technique for controlling the spray mechanism 102 or components thereof in a selected manner.

In an embodiment, the control electrical circuitry 118 is configured to direct the spray mechanism 102 to stop spraying the fluid 112 responsive to a specified operational condition. For example, the specified operational condition includes at least one of spray time, the distance being outside a specified range as sensed by the distance sensor 122, or the distance changing at a rate exceeding a maximum rate as sensed by the distance sensor 122. In other embodiments, the control electrical circuitry 118 directs the spray mechanism 102 to intermittently spray the fluid 112 onto the target region 114. As previously discussed, the specified operational conditions may be pre-programmed into the control electrical circuitry 118 or set by the user.

Figure 2:
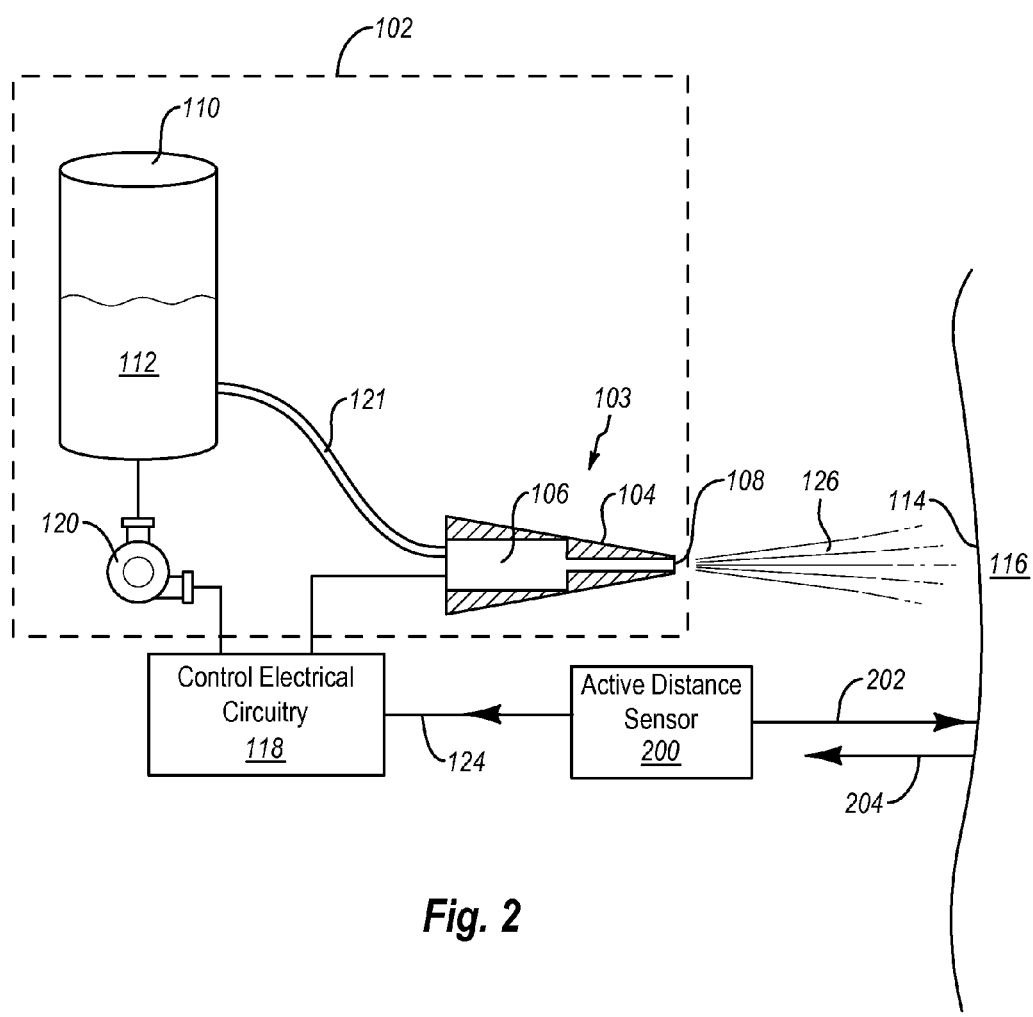
FIG. 2 is a schematic diagram of the fluid spraying apparatus shown in FIG. 1 in which a distance sensor thereof includes at least one active distance sensor according to an embodiment.

FIG. 2 is a schematic diagram of the fluid spraying apparatus 100 shown in FIG. 1 in which the distance sensor 122 thereof includes at least one active distance sensor 200 according to an embodiment. As previous described, the active distance sensor 200 may include at least one of an acoustic sensor that is configured to output an acoustic signal to the target region 114 and receive a reflected acoustic signal therefrom, an optical sensor that is configured to output an optical signal to the target region 114 and receive a reflected optical signal therefrom, or a radar device that is configured to output an electromagnetic signal to the target region 114 and receive a reflected signal therefrom.

In operation, one or more active sensing signals 202 are output from the active distance sensor 200 toward the target region 114 of the subject 116. One or more affected sensing signals 204 are reflected from the target region 114 indicative of the distance of the spray mechanism 102 from the target region 114. As previously discussed, the operation of the spray mechanism 102 may be controlled by the control electrical circuitry 118 responsive to the active distance sensor 200 receiving the one or more affected sensing signals 204 and transmitting information at least related to the distance to the control electrical circuitry 118 based on the one or more affected sensing signals 204 as the one or more sensing signal 124.

Figure 3:
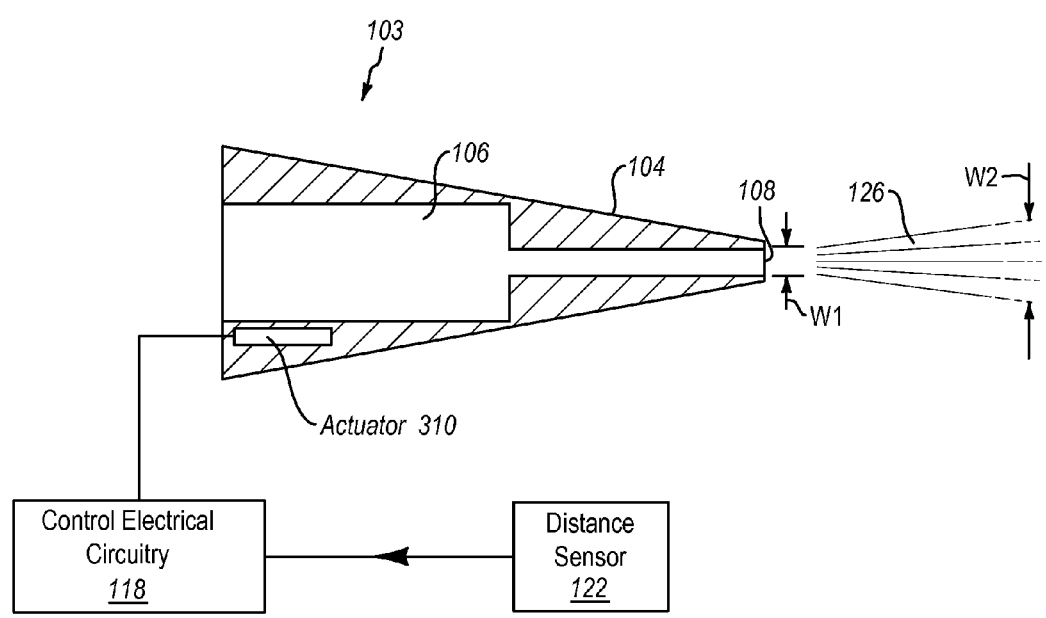
FIG. 3 is a partial schematic diagram of the fluid spraying apparatus shown in FIG. 1 in which a spray mechanism thereof includes an adjustable spray nozzle having an adjustable output orifice according to an embodiment.

FIG. 3 is a partial schematic diagram of the fluid spraying apparatus 100 shown in FIG. 1 in which the output orifice 108 of the adjustable spray nozzle 104 is adjustable according to an embodiment. The spraying device 103 includes an actuator 310 operably coupled to the adjustable spray nozzle 104 that is configured to alter a width W1 of the output orifice 108. In one or more embodiments, the actuator 310 may include at least one of a piezoelectric actuator, a shape-memory-alloy actuator, or an electromagnetic actuator that is configured to alter the width W1 of the output orifice 108 to thereby alter a width W2 of the spray 126 emanating therefrom. For example, the actuator 310 may selectively drive a needle assembly or other obstruction feature within the fluid delivery passageway 106 that either physically or operationally alters the width W1 of the output orifice 108. In another embodiment, the actuator 310 may increase or decrease the width W1 by deploying or undeploying an aperture cover or other obstruction feature.

FIGS. 4A and 4B are partial schematic diagram and plan views, respectively, of the spray mechanism 102 of the fluid spraying apparatus 100 shown in FIG. 1 according to an embodiment. The adjustable spray nozzle 104 includes a plurality of output orifices 108a-108n through and from which the fluid 112 is sprayed during operation. In the illustrated embodiment, the plurality of output orifices 108a-108n may be circumferentially distributed, but other configurations may be employed. Each of the plurality of output orifices 108a-108n is in fluid communication with a corresponding fluid conduit 400a-400n, all of which may be collectively in fluid communication with the one or more fluid conduits 121 coupled to the reservoir 110.

During operation, a droplet size of droplets 402 sprayed from the plurality of output orifices 108a-108n may be controlled by varying the pressure of the fluid 112 pumped to the corresponding fluid conduits 400a-400n associated with each of the plurality of output orifices 108a-108n responsive to the one or more sensing signals 124 (FIG. 1). For example, increasing the pump pressure from the pump 120 may decrease the droplet size of the droplets 402, while decreasing the pump pressure from the pump 120 may relatively increase the droplet size of the droplets 402.

Figure 5:
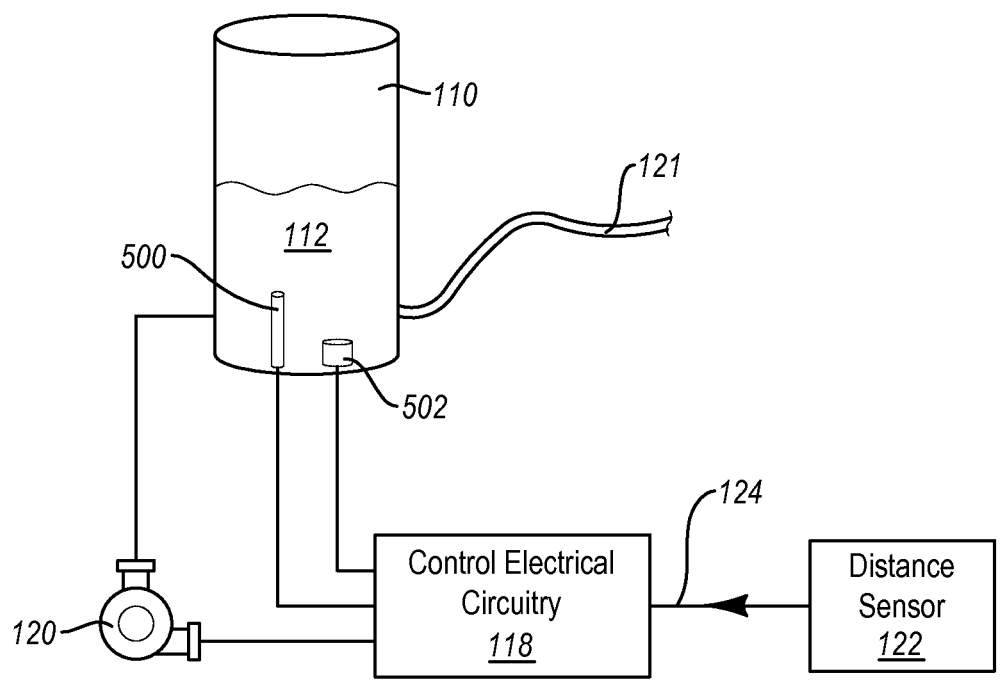
FIG. 5 is a partial schematic diagram of the fluid spraying apparatus shown in FIG. 1 in which a heating element is provided for heating fluid held in a reservoir of the fluid spraying apparatus according to an embodiment.

FIG. 5 is a partial schematic diagram of the fluid spraying apparatus 100 shown in FIG. 1 in which a heating or cooling element 500 is provided for heating or cooling the fluid 112 held in the reservoir 110 according to an embodiment. The heating or cooling element 500 is disposed in the reservoir 110, and operably coupled to the control electrical circuitry 118 which controls the heating or cooling thereof so that a temperature of the fluid 112 may be selectively and accurately controlled responsive to the one or more sensing signals 124 received from the distance sensor 122. For example, the heating or cooling element 500 may include at least one of a resistance heating element, a Peltier cell, or other suitable heating element. A temperature sensor 502 (e.g., a thermal couple or infrared temperature sensor) may also be provided for measuring a temperature of the fluid 112 during or after heating thereof. The temperature sensor 502 is also operably coupled to the control electrical circuitry 118.

During operation, the control electrical circuitry 118 may direct the heating element 500 to controllably heat or cool the fluid 112 to a selected temperature as measured by the temperature sensor 502. In an embodiment, the heating or cooling of the fluid 112 by the heating or cooling element 500 may be responsive to the one or more sensing signals 124 received from the distance sensor 122. For example, if the distance sensed by the distance sensor 122 exceeds a certain distance, the control electrical circuitry 118 may direct the heating or cooling element 500 to increase the temperature of the fluid 112 to be sprayed. Conversely, if the distance sensed by the distance sensor 122 is below a certain distance, the control electrical circuitry 118 may direct the heating or cooling element 500 to decrease the temperature of the fluid 112 to be sprayed. In an embodiment, the heating or cooling of the fluid by the heating element 500 is not responsive to the one or more sensing signals 124 received from the distance sensor 122, but may be responsive to user input via a user interface (e.g., a keypad, touch screen, etc.).

Figure 6:
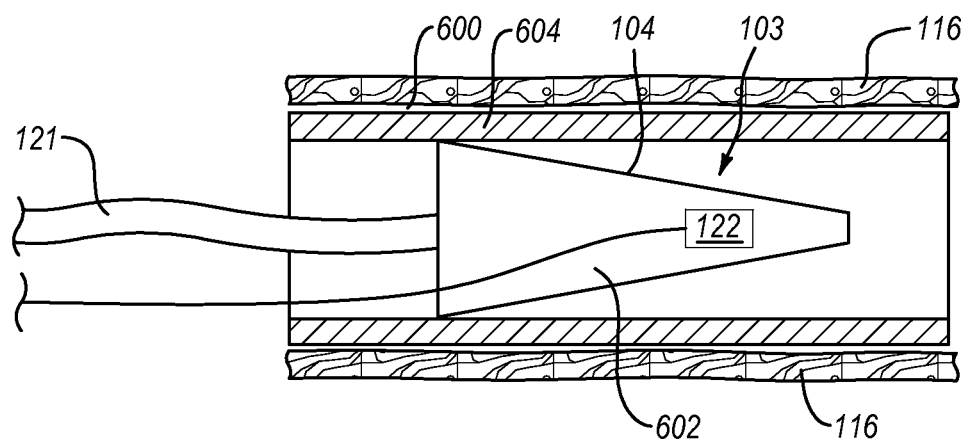
FIG. 6 is a partial schematic diagram of the fluid spraying apparatus shown in FIG. 1 in which a spray mechanism and a distance sensor thereof are integrated and disposed within a delivery catheter for deployment in a subject according to an embodiment.

When the fluid spraying apparatus 100 is to be used for treating internal body tissue of the subject 116, all or some components of the fluid spraying apparatus 100 may compactly disposed in a delivery catheter. FIG. 6 is a partial schematic diagram of the fluid spraying apparatus 100 shown in FIG. 1 in which the spraying device 103 and the distance sensor 122 are integrated with each other for ease of delivery inside a body lumen 600 of the subject 116 according to an embodiment. For example, the distance sensor 122 may be mounted to an exterior 602 of the adjustable spray nozzle 104 of the spraying device in a suitable position so that the distance sensor 122 has an appropriate "field-of-view" of the target region 114 of the subject 116. The integrated assembly of the spraying device 103 and the distance sensor 122 may be compactly disposed within a delivery catheter 604 for deployment in the body lumen 400 of the subject 116. For example, the delivery catheter 604 including the integrated assembly of the spraying device 103 and the distance sensor 122 may be deployed in the body lumen 600 using the Seldinger technique or other suitable technique. For example, the body lumen 600 may be defined by a wall of a vein, blood vessel, organ, or any other portion of the body of the subject 116.

Figure 7:
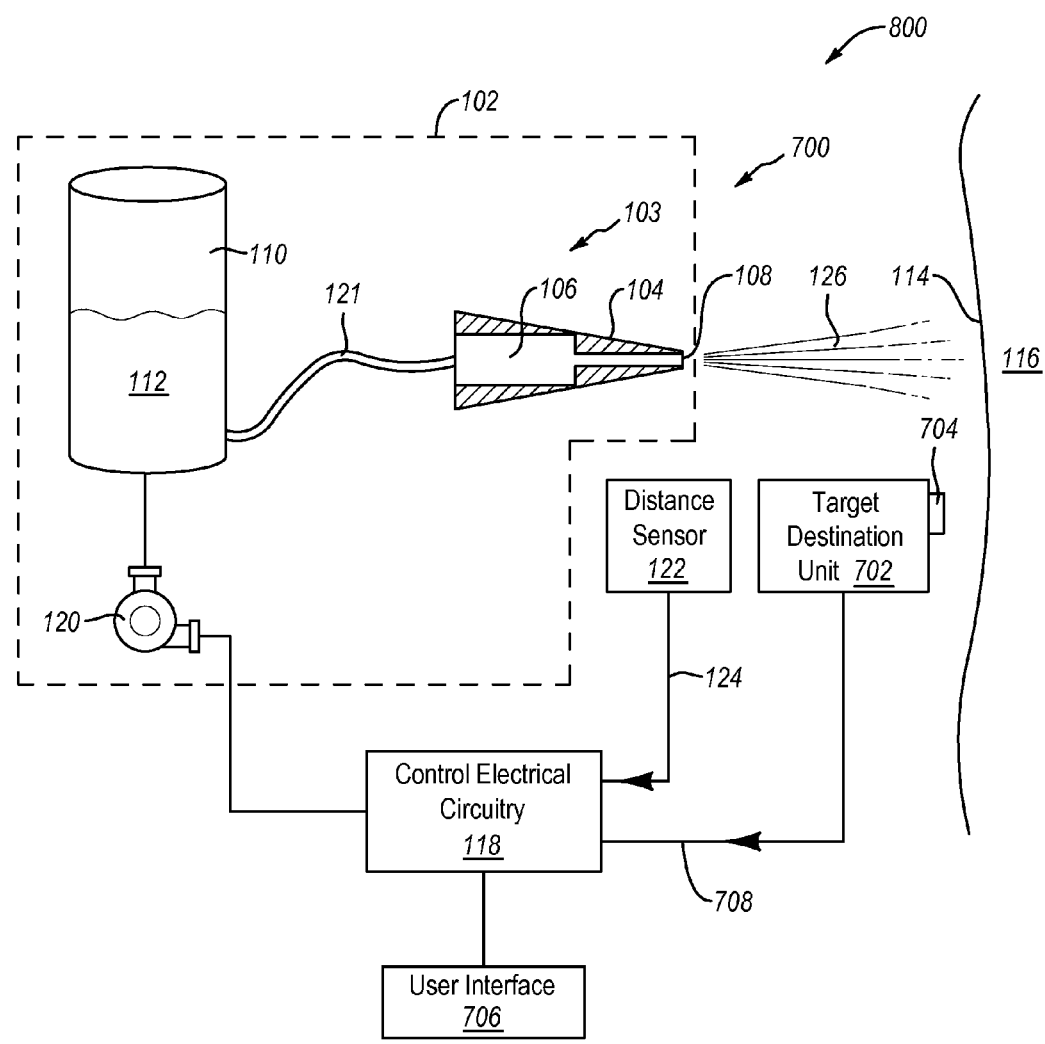
FIG. 7 is a schematic diagram of an embodiment of a fluid spraying apparatus that includes at least one distance sensor and a target designation unit.

FIG. 7 is schematic diagram of an embodiment of a fluid spraying apparatus 700 that includes both at least one distance sensor and a target designation unit for assisting with accurate targeting of the target region 114 of the subject 116. For example, the target designation unit may act in concert with the distance sensor to assist with accurate targeting of the target region 114 of the subject 116. In the interest of brevity, components in both fluid spraying apparatuses 100 and 700 that are identical or similar to each other have been provided with the same reference numerals and an explanation of their structure and function will not be repeated unless the components function differently in the fluid spraying apparatuses 100 and 700.

Like the fluid spraying apparatus 100, the fluid spraying apparatus 700 is suitable for spraying a medically suitable fluid onto a target region of a subject for variety of uses, such as for treating or removing tissue of the subject. However, the fluid spraying apparatus 700 further includes a target designation unit 702 including a target sensor 704 that is configured to sense the target region 114 of the subject 116, and a user interface 706 operably coupled to the control electrical circuitry 118. For example, the user interface 706 may include a suitable user interface, such as a keypad, touch screen, voice command, etc. The target sensor 704 may include one or more of various types of target sensors, such as at least one of a motion sensor (e.g., a MEMS gyroscope) or an image sensor (e.g., an electronic camera). As will be discussed in more detail below, the target designation unit 702 may operate in concert with the distance sensor 122 to accurately target the target region 114 of the subject 116.

In an embodiment, the user interface 706 is configured to enable a user to designate the target region 114, which is communicated to the control electrical circuitry 118. The target sensor 704 is configured to sense the target region 114 of the subject 116 and communicate one or more target sensing signals 708 to the control electrical circuitry 118 and displayed on the user interface 706, such as via an image on a screen. The user may select and designate all or a portion of the target region 114 sensed by the target sensor 704 via the user interface 706. Responsive to the user selecting the target region 114 via the user interface 706, the control electrical circuitry 118 may activate the pump 120 for directing the spray mechanism 102 to spray the spray 126 onto the designated target region 114.

In an embodiment, the user interface 706 is configured for the user to designate the target region 114 responsive to the spray mechanism 102 spraying the target region 114. In an embodiment, the user interface 706 is configured for the user to designate the target region 114 as correct responsive to the spray mechanism 102 spraying the target region 114. In such an embodiment, the control electrical circuitry 118 activates and maintains the spray mechanism 102 spraying the spray 126 on the target region 114 responsive to the target region 114 being designated as correct by the user.

As discussed above, in an embodiment, the target sensor 704 may include a motion sensor configured to sense motion of the spray mechanism 102 and output the one or more target sensing signals 708 encoding data related to the sensed motion to the control electrical circuitry 118. In such an embodiment, the control electrical circuitry 118 may be configured to instruct the spray mechanism 102 to direct the spray 126 onto the target region 114 responsive to the data. For example, as the motion of the spray mechanism 102 is sensed, the operational characteristics of the spray mechanism 102 may be appropriately adjusted by the control electrical circuitry 118, as needed or desired, so that the spray 126 accurately targets the desired target region 114 responsive to the sensed motion of the spray mechanism 102. For example, the adjustable spray nozzle 104 may be steered to account for motion of the spray mechanism 102. In some embodiments, the control electrical circuitry 118 includes memory configured to store the data related to the sensed motion for further review or analysis at a later time.

In an embodiment, the control electrical circuitry 118 is configured to direct the spray mechanism 102 to stop spraying fluid responsive to a specified operational condition. For example, the specified operational condition may include at least one of spray time, tissue damage sensed by the target sensor 704, the distance being outside a specified range as sensed by the distance sensor 122, or the distance changing at a rate exceeding a maximum rate as sensed by the distance sensor 122.

Figure 8:
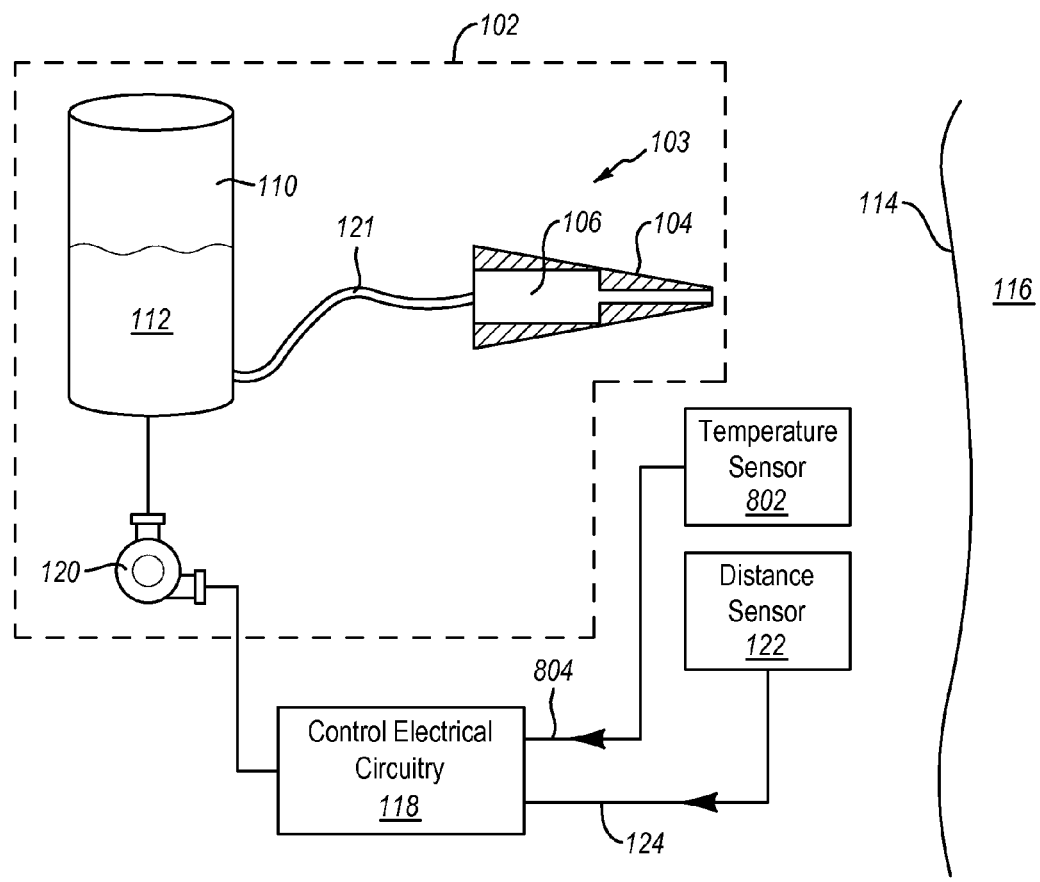
FIG. 8 is a schematic diagram of an embodiment of a fluid spraying apparatus including a temperature sensor configured to sense a temperature of a target region.

FIG. 8 is a schematic diagram of an embodiment of a fluid spraying apparatus 800 including a temperature sensor 802 configured to sense a temperature of the target region 114. In the interest of brevity, components in both fluid spraying apparatuses 100 and 800 that are identical or similar to each other have been provided with the same reference numerals and an explanation of their structure and function will not be repeated unless the components function differently in the fluid spraying apparatuses 100 and 800.

The temperature sensor 802 may be configured to sense a temperature of the target region 114 and communicate the temperature to the control electrical circuitry 118 via one or more temperature sensing signals 804. For example, the temperature sensor 802 may be an infrared sensor or other suitable device configured to measure temperature of the target region 114 without physically contacting the target region 114. The control electrical circuitry 118 is configured to direct the spray mechanism 102 to spray the fluid 112 onto the target region 114 responsive to the temperature sensed by the temperature sensor 802. For example, in an embodiment, the control electrical circuitry 118 is configured to direct the spray mechanism 102 to spray the fluid 112 on the target region 114 until a selected temperature is sensed by the temperature sensor 802. In an embodiment, this embodiment, may be combined with the embodiment shown in FIG. 5 so that the temperature of the fluid 112 may be cooled or heated (as appropriate) via the heating or cooling element 500 to enable imposing the selected temperature on the target region 114.

In an embodiment, the temperature sensor 802 may be remote from the spray mechanism 102 and the spraying device 103. In other embodiments, the temperature sensor 802 may be integrated (e.g., mounted) with the spraying device 103.

In an embodiment, the control electrical circuitry 118 is configured to direct the spray mechanism 102 to stop spraying the fluid 112 responsive to a specified operational condition. For example, the specified operational condition may include at least one of spray time, time that target region 114 is at a selected temperature as sensed by the temperature sensor 802, the distance being outside a specified range as sensed by the distance sensor 122, or the distance changing at a rate exceeding a maximum rate as sensed by the distance sensor 122.

In an embodiment, the control electrical circuitry 118 is configured to direct the spray mechanism 102 to spray the fluid 112 on the target region 114 so that a selected temperature profile is imposed on the target region 114. Such a temperature profile may be measured by the temperature sensor 802, which may be configured as a microwave temperature sensor that outputs microwave energy and determines the temperature from the reflected and/or absorbed microwave energy. For example, the temperature profile may be a three-dimensional temperature profile, a temperature-time profile, a temperature-depth profile, or a temperature-time-depth profile.

The temperature profile may be controlled or imposed by various techniques. For example, the control electrical circuitry 118 may be configured to direct adjusting the adjustable spray nozzle 104 to alter at least one of a spray rate of the fluid 112 or a pulse spray frequency of the fluid 112 for controlling the selected temperature profile.

In other embodiments, the operation of the spray mechanism 102 may be terminated responsive to feedback from the temperature sensor 802 or other additional sensors. For example, the control electrical circuitry 118 may terminate operation of the spray mechanism 102 responsive to at least one of temperature sensed by the temperature sensor 802, tissue damage of the target region 114 sensed by an additional sensor (e.g., an image sensor, or chemical sensor), or optical characteristics of the target region sensed by an optical sensor (e.g., an infrared sensor).

Figure 9:
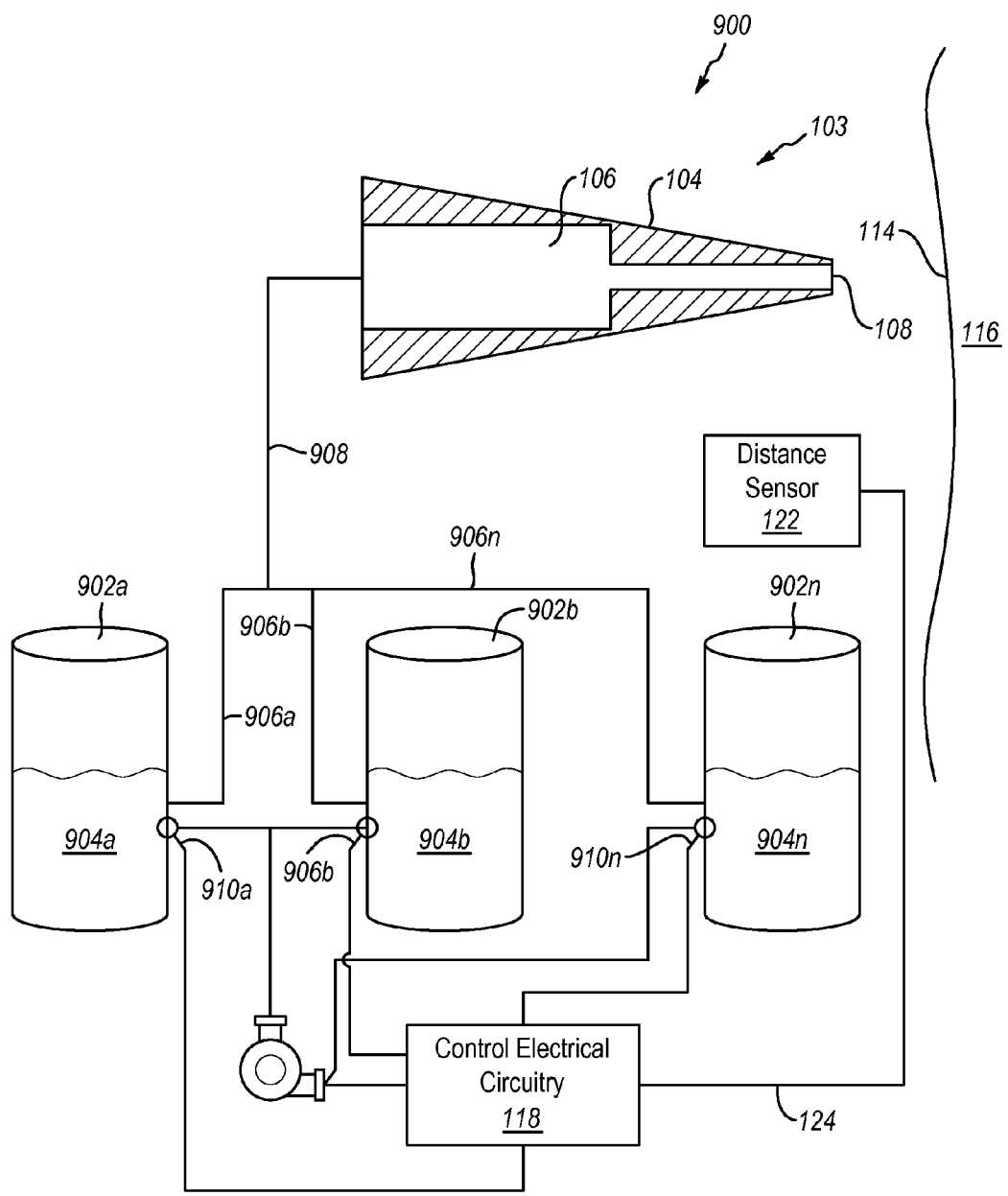
FIG. 9 is a schematic diagram of an embodiment of a fluid spraying apparatus including a plurality of reservoirs from which fluid may be selectively sprayed onto a target region of a subject.

FIG. 9 is a schematic diagram of an embodiment of a fluid spraying apparatus 900 including a plurality of reservoirs 902a-902n from which fluid may be selectively sprayed onto the target region 114 of the subject 116. In the interest of brevity, components in both fluid spraying apparatuses 100 and 900 that are identical or similar to each other have been provided with the same reference numerals and an explanation of their structure and function will not be repeated unless the components function differently in the fluid spraying apparatuses 100 and 900.

Each of the plurality of reservoirs 902a-902n may hold a corresponding fluid 904a-904n therein that may have a different composition or maintained at a different temperature. For example, the fluids 904a-904n held in the corresponding reservoirs 902a-902n may be chosen from any of the fluids disclosed herein for the fluid 112, such as a liquid, a gas, an aerosol, a cryogen, or a fluid having a temperature greater than about 45° C. (i.e., a pyrofluid). Each of the reservoirs 902a-902n may be operably coupled to the pump 120. Fluid conduits 906a-906n may fluidly couple the fluids 904a-904n in the corresponding reservoirs 902a-902n to the fluid delivery passageway 106 of the adjustable spray nozzle 104 via a common fluid conduit 908.

The pump 120 may be operably coupled to each of the reservoirs 902a-902n via corresponding valves 910a-910n. For example, each of the valves 910a-910n may be electronically-actuatable valves that may be selectively electronically actuated by the control electrical circuitry 118.

In operation, responsive to the one or more sensing signals 124 generated by the distance sensor 122, the control electrical circuitry 118 may selectively actuate the valves 910a-910n so that the fluids 904a-904n in the corresponding reservoirs 902a-902n may be selectively pumped by the pump 120 to the fluid delivery passageway 106 of the adjustable spray nozzle 104 via the common fluid conduit 908.

For example, in an embodiment, the fluids 904a-904n may be sequentially sprayed onto the target region 114. In a more detailed embodiment, the fluid 904a may be cryogen, while the fluids 904b and 904n may be pyrofluids maintained at different respective temperatures. In such an embodiment, the pyrofluids may first be sequentially sprayed onto the target region 114 followed by spraying the cryogen or vice versa.

Figure 10:
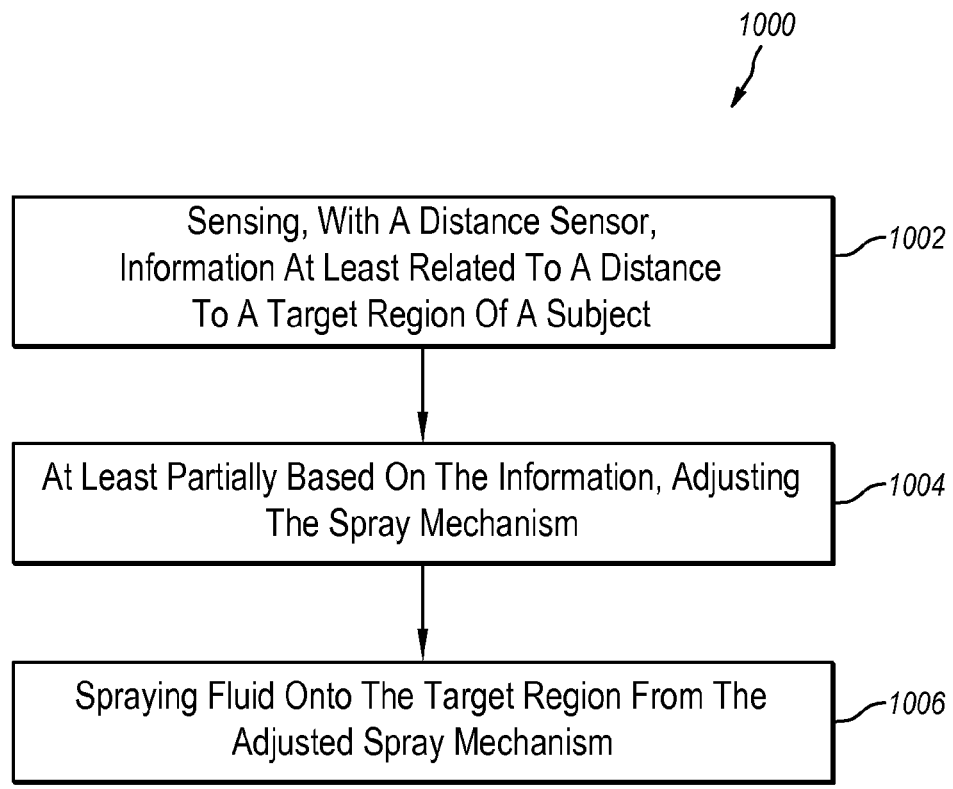
FIG. 10 is a flow diagram of an embodiment of an operating method that may be implemented using any of the fluid spraying apparatuses disclosed herein.

FIG. 10 is a flow diagram of an embodiment of an operating method 1000 that may be implemented using any of the fluid spraying apparatuses disclosed herein, such as the fluid spraying apparatuses described in relation to FIGS. 1-9. The method 1000 is directed to a method of adjusting a spray mechanism of a fluid spraying apparatus. The method 1000 includes an act 1002 of sensing, with a distance sensor (e.g., the distance sensor 122), information at least related to a distance to a target region of a subject. The method 1000 further includes an act 1004 of at least partially based on the information, adjusting the spray mechanism (e.g., the adjustable spray nozzle 104 or the pump 120) and an act 1006 of spraying fluid onto the target region from the adjusted spray mechanism. For example, as previously discussed, the target region may be internally or externally located on the subject.

In an embodiment, the act 1002 of sensing may include sensing the information with an active distance sensor. In other embodiments, the act 1002 of sensing may include sensing the information with a passive distance sensor. In an embodiment, the method 1000 further includes heating the fluid prior to being sprayed responsive to the distance sensed.

In an embodiment, the act 1004 of adjusting the spray mechanism may include at least one of adjusting the spray nozzle to alter a spray width of the fluid to be sprayed, adjusting the spray mechanism includes adjusting the spray mechanism to alter a fluid pressure of the fluid to be sprayed, adjusting the spray mechanism to alter a focus of the spray nozzle, adjusting the spray mechanism to alter a droplet size of the fluid to be sprayed, or adjusting the spray mechanism to substantially maintain a target arrival diameter of the fluid sprayed as the distance changes.

In another embodiment that may be used in combination with any of the foregoing adjusting techniques, the act 1006 of spraying fluid may include spraying fluid onto the target region from the adjusted spray mechanism intermittently or with a substantially constant spray. In other embodiments, the act 1006 of spraying fluid onto the target region from the adjusted spray mechanism may include sequentially spraying cryogen and a pyrofluid onto the target region, such as previously described in connection with the embodiment shown in FIG. 9.

In an embodiment, the act 1004 of adjusting the spray mechanism may include (1) determining one or more operational characteristics of the spray mechanism (e.g., the spray nozzle or pump) to be adjusted at least partially based on the distance; (2) adjusting the one or more operational characteristics of the spray mechanism at least partially based on the determined one or more operational characteristics; and (3) directing the spray mechanism having the one or more adjusted operational characteristics to spray the fluid onto the target region.

In an embodiment, the method 1000 may further include employing a target designation unit to assist with accurately targeting the target region with the spray of fluid. For example, the method 1000 may further include sensing the target region with a target designation unit (e.g., the target designation unit 702), designating the target region, and spraying the fluid onto the target region responsive to the target region being designated.

In another embodiment, the act 1006 of spraying the fluid onto the target region may be responsive to feedback from a temperature sensor. For example, the method 1000 may further include an act of sensing a temperature of the target region of the subject with a temperature sensor, and the act 1006 may include spraying the fluid onto the target region responsive to the temperature being sensed.

Figure 11:
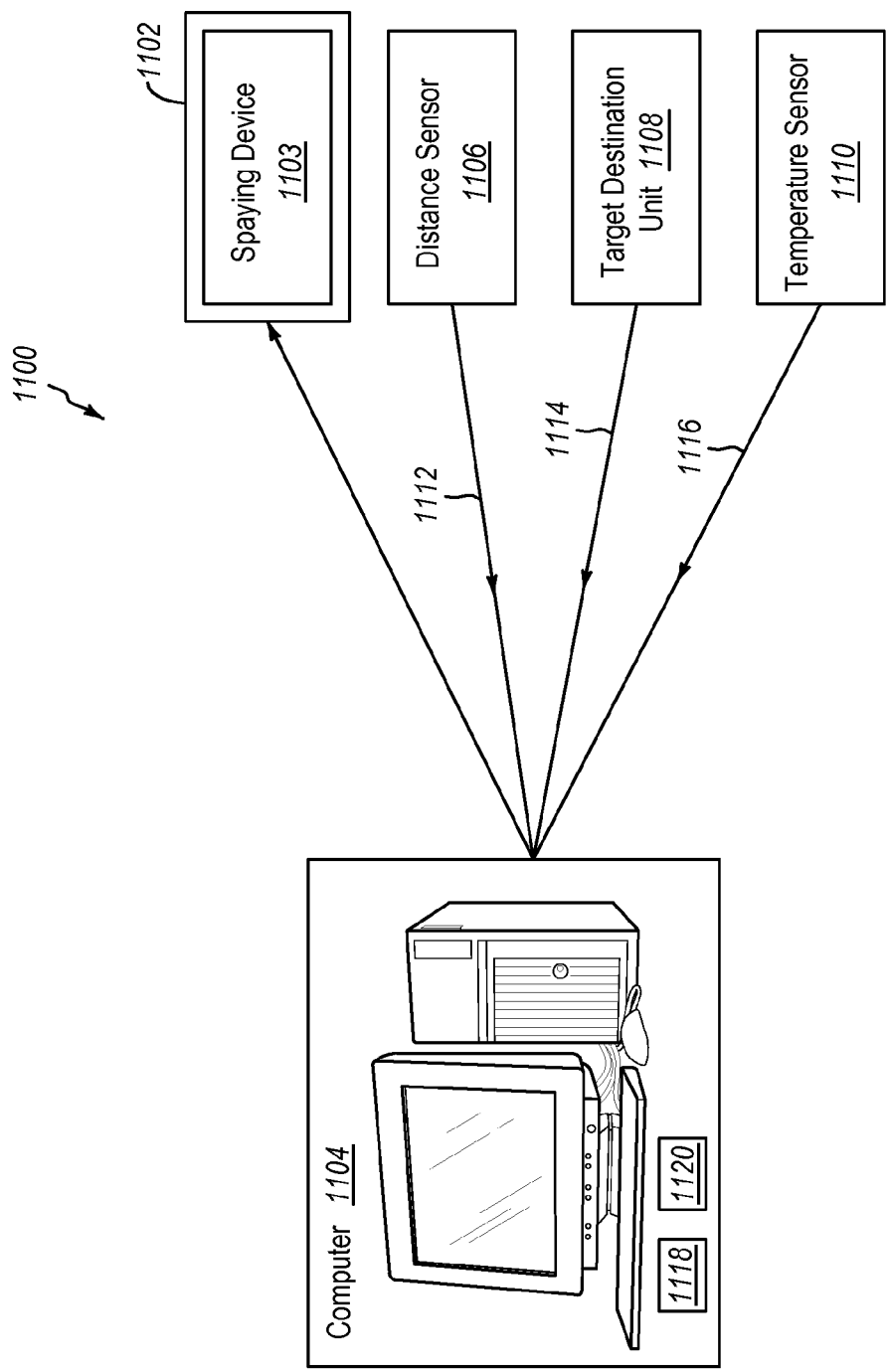
FIG. 11 is a schematic diagram of an embodiment of a system including a fluid spraying apparatus and a computer for controlling the fluid spraying apparatus.

FIG. 11 is a schematic diagram of an embodiment of a system 1100 including a fluid spraying apparatus 1102 having a spraying device 1103 and a computer 1104 for controlling the fluid spraying apparatus 1102. The system 1100 further includes at least one distance sensor 1106 and an optional target designation unit 1108 and an optional temperature sensor 1110. The distance sensor 1106, the target designation unit 1108, and the temperature sensor 1110 are structured and function the same or similar to those components previously described in relation to FIGS. 1, 2, 7, and 8.

For example, the distance sensor 1106 may output one or more distance sensing signals 1112 indicative of a distance that the fluid spraying apparatus 1102 is from a target region, the target designation unit 1108 may output one or more target sensing signals 1114, the temperature sensor 1110 may output one or more temperature sensing signals 1116 indicative of a temperature of the target region. The spraying device 1103 may be configured as any of the spraying devices disclosed herein.

The distance sensor 1106, the target designation unit 1108, and the temperature sensor 1110 may be remote from the fluid spraying apparatus 1102 or may integrated with the fluid spraying apparatus 1102. Additionally, the distance sensor 1106, the target designation unit 1108, and the temperature sensor 1110 may be wirelessly coupled or electrically coupled via a wired connection to the computer 1104.

The computer 1104 may be any suitable desktop computer, laptop computer, or other suitable computing platform, which is operably coupled to the fluid spraying apparatus 1102 and the distance sensor 1106, the optional target designation unit 1108, and the optional temperature sensor 1110. The computer 1104 may include at least one processor 1118 and memory 1120 storing instructions that when executed by the processor 1118 activates the fluid spraying apparatus 1102 (e.g., the spraying device 1103 of the fluid spraying apparatus 1102) responsive to receiving the one or more distance sensing signals 1112, the optional one or more target sensing signals 1114, or the optional one or more temperature sensing signals 1116.

In an embodiment, the computer 1104 may be remote from the fluid spraying apparatus 1102, such as in another room or another section of the same room. In an embodiment, the computer 1104 may be integrated with the fluid spraying apparatus 1102 similar to the manner in which the control electrical circuitry 118 forms part of the fluid spraying apparatus 100.

The instructions stored in the memory 1120 may be for implementing any of the modification/adjusting of the spray mechanism 1103 operational characteristics as previously discussed in the embodiments shown and described in FIGS. 1-10. For example, the memory 1120 may include instructions that when executed by the at least one processor 1118 cause the fluid spraying apparatus 1102 to perform any of the method described in connection with FIG. 10. As such, the control electrical circuitry 118 previously discussed may be considered to constitute part of or all of the processor 1118 and the memory 1120. For example, responsive to the one or more distance sensing signals 1112, the computer 1104 may direct altering a number of different operational characteristics of the fluid spraying apparatus 1102. For example, during operation, the computer 1104 may direct the spraying device 1103 to alter a spray width of the spray responsive to receiving the one or more distance sensing signals 1112. For example, during operation, the computer 1104 may direct the fluid spraying apparatus 1102 to alter a fluid pressure of the fluid sprayed responsive to receiving the one or more distance sensing signals 1112. As another example, during operation, the computer 1104 may direct the spraying device 1103 to alter a fluid focus thereof responsive to receiving the one or more distance sensing signals 1112. As yet another example, during operation, the computer 1104 may direct the fluid spraying apparatus 1102 to alter a droplet size of the spray responsive to receiving the one or more distance sensing signals 1112 by increasing or decreasing the applied pressure exerted on the fluid to be sprayed.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." The reader will recognize that "configured to" can generally encompass active-state components and/or inactive-state components and/or standby-state components, etc. unless context requires otherwise.

In some instances, one or more components may be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A fluid spray apparatus for treating a target region of at least one tissue of a subject with a fluid comprising a cryogen or a pyrofluid, the fluid spraying apparatus comprising:
    a spray mechanism including,
        at least one reservoir holding the fluid comprising the cryogen or the pyrofluid;
        a spraying device operably coupled to the at least one reservoir, the spraying device including,
            an adjustable spray nozzle including an elongated nozzle body having a passageway extending therethrough that is fluidly connected to the at least one reservoir, the passageway terminating in an output orifice;
            an obstruction feature deployable within the passageway to alter a width of the output orifice; and
            a nozzle actuator configured to deploy the obstruction feature;
    a distance sensor configured to sense information at least related to a distance to a target region of the at least one tissue of the subject from the output orifice of the adjustable spray nozzle, and output one or more signals encoding the information; and
    a computing device including,
        control electrical circuitry coupled to the spray mechanism, the nozzle actuator, and the distance sensor, wherein the nozzle actuator is operably coupled to the spray nozzle and the nozzle actuator is configured to adjust the width of the output orifice of the adjustable spray nozzle responsive to receiving one or more signals indicating the distance between the output orifice and the target region; and
        non-transitory memory operably coupled to the control electrical circuitry, the non-transitory memory for storing data encoding instructions for the activation or control of the spray mechanism including directing the nozzle actuator to controllably adjust the width of the out orifice of the adjustable spray nozzle by deploying or undeploying the obstruction feature to adjust an area of the target region that is sprayed by the fluid from the output orifice of the adjustable spray nozzle.

2. The fluid spraying apparatus of claim 1, wherein the distance sensor includes at least one active distance sensor.

3. The fluid spraying apparatus of claim 2, wherein the at least one active distance sensor includes at least one of an acoustic sensor, an optical sensor, ultrasonic sensor, or a radar device.

4. The fluid spraying apparatus of claim 1, wherein the distance sensor includes at least one passive distance sensor.

5. The fluid spraying apparatus of claim 4, wherein the at least one passive distance sensor includes an image sensor.

6. The fluid spraying apparatus of claim 1, wherein:
    the at least one reservoir includes a fluid including at least one of cryogen or a pyrofluid;
    the distance sensor includes an image sensor positioned and configured to image subsurface vasculature features of the target region of the subject; and
    the control electrical circuitry is configured to direct the spray mechanism to spray the fluid onto the target region to affect the subsurface vasculature features.

7. The fluid spraying apparatus of claim 1, wherein the control electrical circuitry is configured to direct the adjustable spray nozzle to alter a spray width of the fluid sprayed therefrom responsive to receiving the one or more signals.

8. The fluid spraying apparatus of claim 1, wherein the control electrical circuitry is configured to direct the spray mechanism to alter a fluid pressure of the fluid sprayed therefrom responsive to receiving the one or more signals.

9. The fluid spraying apparatus of claim 1, wherein the control electrical circuitry is configured to direct the adjustable spray nozzle to alter a fluid focus thereof responsive to receiving the one or more signals.

10. The fluid spraying apparatus of claim 1, wherein the control electrical circuitry is configured to direct the spray mechanism to alter a droplet size of the fluid sprayed therefrom responsive to receiving the one or more signals.

11. The fluid spraying apparatus of claim 1, wherein the control electrical circuitry is configured to direct adjusting the adjustable spray nozzle to substantially maintain a target arrival diameter of the fluid sprayed therefrom responsive to receiving the one or more signals.

12. The fluid spraying apparatus of claim 1, wherein the spray mechanism is configured to adjust at least one of a spray width of the fluid sprayed, a fluid pressure of the fluid sprayed, a fluid focus of the adjustable spray nozzle, an output orifice of the adjustable spray nozzle, or a droplet size of the fluid sprayed.

13. The fluid spraying apparatus of claim 1, wherein the adjustable spray nozzle includes an atomizing adjustable spray nozzle or a pressure-swirl spray nozzle.

14. The fluid spraying apparatus of claim 1 wherein the control electrical circuitry is configured to:
determine one or more operational characteristics of the adjustable spray nozzle to be adjusted at least partially based on the information;
adjust the one or more operational characteristics of the adjustable spray nozzle at least partially based on the determined one or more operational characteristics; and
direct the spray mechanism having the adjustable spray nozzle configured with the one or more adjusted operational characteristics to spray fluid onto the target region.

15. The fluid spraying apparatus of claim 14, wherein the one or more operational characteristics include at least one of pressure of the fluid sprayed, droplet size of the fluid sprayed, or geometry of the fluid sprayed.

16. The fluid spraying apparatus of claim 1, wherein the reservoir includes a fluid that includes a cryogen or a fluid having a temperature greater than about 45° C.

17. The fluid spraying apparatus of claim 16, wherein the cryogen includes at least one of nitrogen, carbon dioxide, a fluorocarbon, ethynol, or ethanol.

18. The fluid spraying apparatus of claim 1, wherein the fluid includes at least one of a liquid, a gas, or an aerosol.

19. The fluid spraying apparatus of claim 1, further comprising a heater positioned and configured to heat the fluid.

20. The fluid spraying apparatus of claim 1, further comprising a delivery catheter housing at least the distance sensor and the spray mechanism.

21. The fluid spraying apparatus of claim 1, further comprising:
a target designation unit including a target sensor configured to sense a target region of the subject; and
wherein the control electrical circuitry is operably coupled to the target designation unit, and configured to activate the spray mechanism responsive to the target sensor sensing the target region.

22. The fluid spraying apparatus of claim 21, wherein the control electrical circuitry controller is operably coupled to a user interface, the user interface configured to receive input designating the target region and communicate the input to the control electrical circuitry.

23. The fluid spraying apparatus of claim 21, wherein the control electrical circuitry is configured to direct the spray mechanism to stop spraying fluid responsive to the target sensor detecting a specified condition.

24. The fluid spraying apparatus of claim 21, wherein:
the target designation unit includes a motion sensor configured to sense motion of the spray mechanism and output one or more motion signals encoding motion data related to the sensed motion to the computing device; and
the non-transitory memory is configured to receive and store the one or more motion signals encoding the motion, data; and
the control electrical circuitry configured to instruct the spray mechanism to direct the spray of the fluid responsive to receiving the motion data.

25. The fluid spraying apparatus of claim 1, further comprising:
a temperature sensor configured to sense a temperature of the target region and communicate the temperature to the control electrical circuitry; and
the control electrical circuitry is configured to direct the spray mechanism to spray fluid on the target region responsive to the temperature sensed by the temperature sensor.

26. The fluid spraying apparatus of claim 25, wherein the control electrical circuitry is configured to direct the spray mechanism to spray the fluid on the target region until a selected temperature is sensed by the temperature sensor.

27. The fluid spraying apparatus of claim 25, wherein the control electrical circuitry is configured to direct the spray mechanism to spray the fluid on the target region so that a selected temperature profile is imposed on the target region.

28. The fluid spraying apparatus of claim 27, wherein the control electrical circuitry is configured to direct adjusting the adjustable spray nozzle to alter at least one of a spray rate of the fluid or a pulse spray frequency of the fluid for controlling the selected temperature profile.

29. The fluid spraying apparatus of claim 25, wherein the control electrical circuitry is configured to terminate operation of the spray mechanism responsive to at least one of the temperature sensed by the temperature sensor, tissue damage of the target region sensed by an additional sensor, or optical characteristics of the target region sensed by an optical sensor.

30. The fluid spraying apparatus of claim 1, wherein the control electrical circuitry is configured to direct the spray mechanism to stop spraying fluid responsive to a specified condition.

31. The fluid spraying apparatus of claim 30, wherein the specified condition includes at least one of spray time, tissue damage, time that target region is at a selected temperature, the distance being outside a specified range, or the distance changing at a rate exceeding a maximum rate.

32. The fluid spraying apparatus of claim 1, wherein:
the at least one reservoir includes a first reservoir holding cryogen and a second reservoir holding a pyrofluid having a temperature greater than 45° C.; and
the control electrical circuitry is configured to direct the spray mechanism to sequentially spray the cryogen and the pyrofluid onto the target region.

33. The fluid spraying apparatus of claim 1, wherein the passageway through the elongated nozzle body terminates at a single output orifice.

34. The fluid spraying apparatus of claim 1, wherein the obstruction feature includes a needle.

35. The fluid spraying apparatus of claim 1, wherein the obstruction feature includes a cover.

36. The fluid spraying apparatus of claim 1, wherein the adjustable spray nozzle includes the nozzle actuator.

37. A system for treating a target region of at least one tissue of a subject with a fluid comprising a cryogen or a pyrofluid, the system, comprising:
a distance sensor configured to sense information at least related to a distance to the target region of the at least one tissue of the subject and output one or more signals encoding the information;
a fluid spraying apparatus operably coupled to the distance sensor, the fluid spraying apparatus including,
a spray mechanism including,
at least one reservoir holding the fluid comprising the cryogen or the pyrofluid;
a spraying device operably coupled to the at least one reservoir, the spraying device including an adjustable spray nozzle including an elongated nozzle body having a passageway extending therethrough that is fluidly connected to the at least one reservoir, the passageway terminating in an output orifice;

an obstruction feature deployable within the passageway to alter a width of the output orifice; and a nozzle actuator configured to deploy the obstruction feature;

a delivery catheter housing the distance sensor and the spraying device therein; and a computer operably the spray mechanism, the nozzle actuator, and the distance sensor, the computer including a non-transitory computer readable medium for storing instruction data encoding instructions that are capable of directly activating or controlling the spray mechanism responsive to receiving one or more signals from the distance sensor indicating distance data including at least the distance between the output orifice and the target region;

wherein the activating or controlling of the spray mechanism includes the computer using the instruction data to direct the nozzle actuator to controllably adjust the width of the output orifice of the adjustable spray nozzle by deploying or undeploying the obstruction feature to adjust an area of the target region that is sprayed by the fluid from the adjustable spray nozzle.

38. The system of claim 37, wherein the obstruction feature includes a needle.

39. The system of claim 37, wherein the obstruction feature includes a cover.

40. The system of claim 37, wherein the adjustable spray nozzle includes the nozzle actuator.

* * * * *